United States Patent
Cribbs et al.

(10) Patent No.: US 6,679,120 B1
(45) Date of Patent: Jan. 20, 2004

(54) SYSTEM AND METHOD FOR GUIDED BORING OBSTACLE DETECTION

(75) Inventors: Robert W. Cribbs, Placerville, CA (US); Ching-Chen Wu, Folsom, CA (US); Douglas G. Niessen, Folsom, CA (US)

(73) Assignee: Gas Research Institute, Des Plaines, IL (US)

( * ) Notice: Subject to any disclaimer, the term of this patent is extended or adjusted under 35 U.S.C. 154(b) by 0 days.

(21) Appl. No.: 10/195,708

(22) Filed: Jul. 15, 2002

(51) Int. Cl.[7] ............................................. G01R 33/20
(52) U.S. Cl. ................................................. 73/598
(58) Field of Search ......................... 73/597, 598, 592, 73/628, 587, 591, 594

(56) References Cited

U.S. PATENT DOCUMENTS 5,457,995 A * 10/1995 Staton et al. ............... 73/596
6,161,434 A * 12/2000 Fink et al. .................. 73/587

* cited by examiner

*Primary Examiner*—Hezron Williams
*Assistant Examiner*—Tamiko Bellamy
(74) *Attorney, Agent, or Firm*—Mark E. Fejer

(57) ABSTRACT

A method and system for detecting an underground obstacle in which a plurality of acoustic signal sensors are deployed in a predetermined pattern on an area of ground defined by a guided drill path. A drill head of a drill is inserted into the ground and a borehole is drilled in the ground along the guided drill path. The noise signal generated by the drill head is detected at at least two of the acoustic signal sensors and the difference in arrival time of the noise signal at the two acoustic signal sensors is determined. This difference in arrival time of noise signal is analyzed, whereby the presence or absence of an underground obstacle is determined.

11 Claims, 5 Drawing Sheets

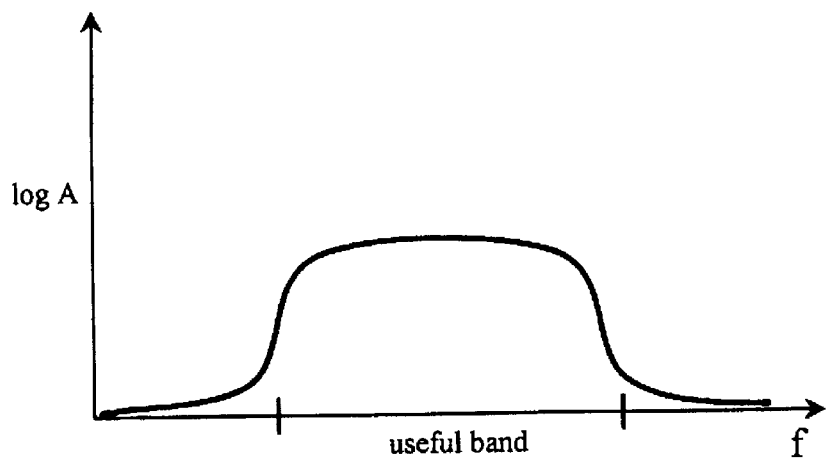
Fig. 7
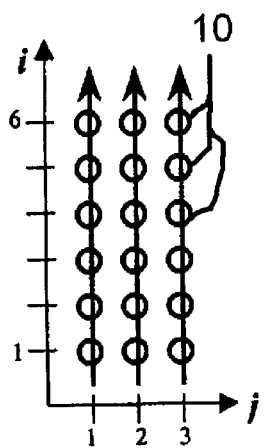 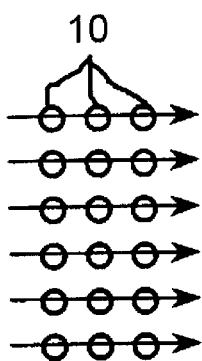 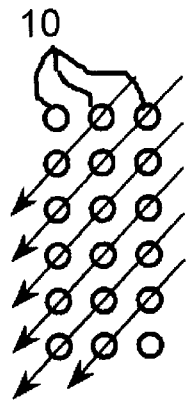 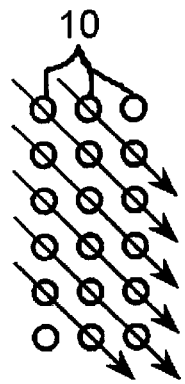
along drill axis    normal to drill axis    45° to left    45° to right
Fig. 8A    Fig. 8B    Fig. 8C    Fig. 8D

Fig. 9
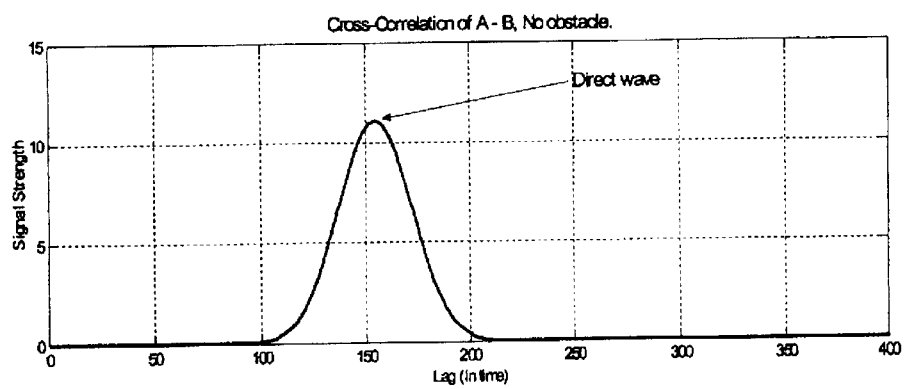
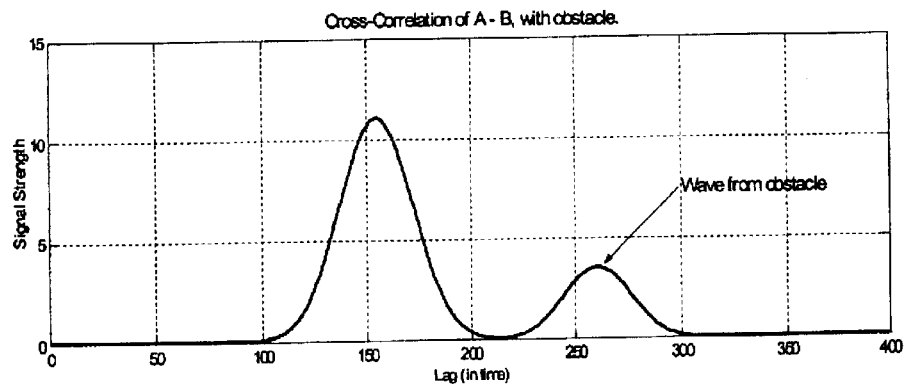
Fig. 10

SYSTEM AND METHOD FOR GUIDED BORING OBSTACLE DETECTION

BACKGROUND OF THE INVENTION

1. Field of the Invention

This invention relates to a method and apparatus for detecting underground obstacles, in particular, plastic pipe encountered in the path of guided drilling operations. More particularly, this invention relates to a method and apparatus for detecting underground obstacles by using the sound generated by the guided drill head that is reflected off the obstacle. This sound is then detected by sensors and analyzed.

2. Description of Related Art

Many underground utilities are installed by drilling a hole and pulling the utility through (guided directional drilling). In some cases, it is possible for the drill to penetrate existing utilities, thereby causing, for example, a gas leak that might cause damage, injury or even death. In other cases, gas lines could inadvertently be installed through sewer or other utility pipes. In the process of clearing the sewer pipe, the gas lines could be broken. This would fill the sewer pipe with gas that could be carried to several buildings, leading to explosions that could cause damage, injury, or death.

Using the current state of the art technology, underground objects are detected using acoustics or ultrasound by transmitting a pulse into the ground and sensing the return echo from the underground object. The time of the echo return in conjunction with the propagation velocity of the pulse provides the distance to the object, and the beam shape or triangulation or image reconstruction determines the lateral position of the object. However, such methods are not suitable for use in connection with simultaneous drilling operations as the amount of noise generated by the drilling operation is likely to interfere with the detection process. Accordingly, it is clear that there is need for a technology capable of detecting underground obstacles, in particular, utility pipes in the path of underground drilling simultaneously with the drilling operation.

SUMMARY OF THE INVENTION

Accordingly, it is one object of this invention to provide a method for detecting the presence of an underground object in the path of an underground drilling operation.

It is another object of this invention to provide a method for avoiding contact with underground obstacles during drilling operations.

It is yet a further object of this invention to provide a system for detecting the presence of an underground object in the path of an underground drilling operation.

These and other objects of this invention are addressed by a method for detecting an underground obstacle in which a plurality of acoustic signal sensors are deployed in a predetermined pattern on an area of ground defined by a guided drill path having a drill head insertion point. The drill head of a drill is inserted into the ground at the drill head insertion point after which drilling of a borehole in the ground along the guided drill path is commenced. A noise signal generated by the drill head is detected at at least two of the acoustic signal sensors and a difference in arrival time of the noise signal at the at least two acoustic signal sensors is determined. The difference in arrival times of the noise signal is then analyzed, whereby the presence or absence of the underground obstacle is determined. Obstacles that are not normal to the direction of the drilling operation, such as pipes that are oriented in a skew direction, are detected by using two or more rows of acoustic signal sensors and processing the signals to detect and locate off-axis pipes. The obstacles to be detected may be under roads or sidewalks of concrete or other materials. In these instances, the acoustic signal sensors can be placed on the surface of these materials to detect the obstacles.

The system for detecting the presence of an underground object in the path of an underground drilling operation in accordance with this invention comprises at least one noise signal generator adapted for drilling boreholes in the ground along a guided drill path, that is, a drill head of a drill, a plurality of acoustic signal sensors disposed in a predetermined pattern on an area of ground defined by the guided drill path, means for measuring an arrival time of the noise signal generated by said noise signal generator at each of the plurality of acoustic signal sensors, and obstacle means for determining the presence or absence of the underground obstacle in the guided drill path using a difference in the arrival time of the noise signal between at least two of the plurality of acoustic signal sensors. The key to the system of this invention is that no other type of noise signal generator is required to carry out the method of this invention.

BRIEF DESCRIPTION OF THE DRAWINGS

These and other objects and features of this invention will be better understood from the following detailed description taken in conjunction with the drawings wherein:

FIG. 7 is a diagram showing a signal spectrum after normalization;

FIGS. 8A–8D are diagrams showing various analysis patterns suitable for use in the method of this invention;

FIG. 9 is a diagram showing the results of cross-correlation in accordance with the method of this invention where no obstacle is present; and FIG. 10 is a diagram showing the results of cross-correlation in accordance with the method of this invention where an obstacle is present.

DETAILED DESCRIPTION OF THE PRESENTLY PREFERRED EMBODIMENTS

Figure 1:
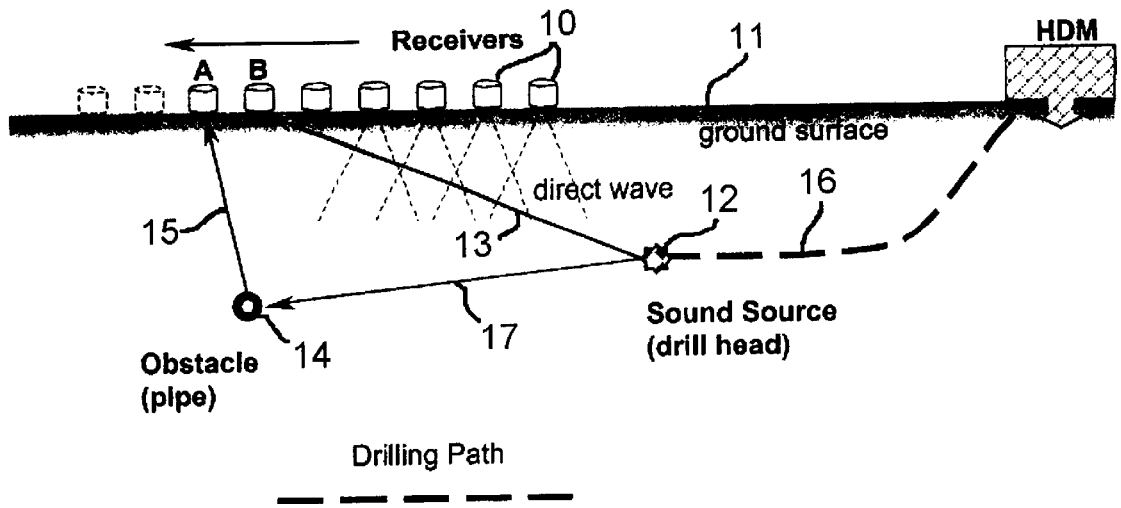
FIG. 1 is a conceptual diagram of the method for detecting underground obstacles in accordance with one embodiment of this invention.

A key feature of the method of this invention is the utilization of the noise created by the drill head as the acoustic signal to detect obstacles in the path of the drill head. As shown in FIG. 1, the method of this invention includes placement of a plurality of acoustic signal sensors or receivers 10 on the surface 11 of the earth ahead of the drill head 12. These sensors detect the direct acoustic wave 13 generated by the drill head 12. If there is an obstacle 14, such as a utility pipe, in the path of the drill head 12, the acoustic signal sensors 10 also detect the acoustic reflection 15 from the obstacle 14. The acoustic signals are then analyzed, as discussed hereinbelow, to determine the presence and location of the obstacle.

In accordance with the method of this invention, a plurality of acoustic signal sensors 10 are deployed in a predetermined pattern on an area of ground defined by an anticipated guided drill path. A drill head 12 of a drill is inserted into the ground at a location on the anticipated guided drill path upstream of the array of acoustic signal sensors 10. As used herein, the location of "upstream" is determined based upon the direction of drilling. Thus, because drilling is occurring in the direction of the array of acoustic signal sensors 10, the point at which the drilling operation is initiated would be considered to be upstream of the sensor array. Drilling to produce a borehole is then commenced along the guided drill path 16. The noise signal generated by the drill head 12 is detected by the acoustic signal sensors 10 and the difference in arrival time of the noise signal at at least two of the acoustic signal sensors 10 (for example, sensor A and sensor B in FIG. 1) is determined. Based upon analysis of the difference in arrival time of the noise signal the presence or absence of an underground obstacle can be determined.

Figure 2:
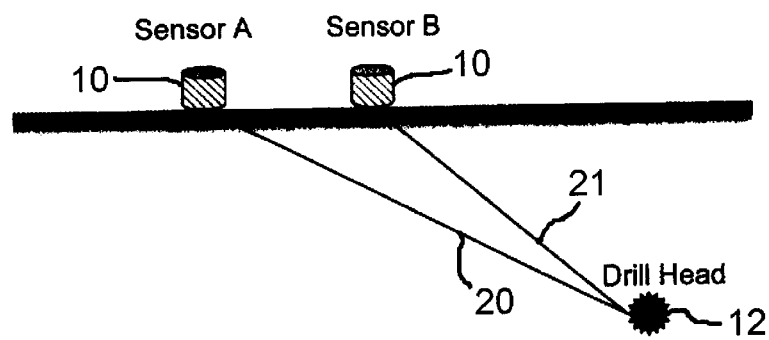
FIG. 2 is a diagram showing the principle of operation of the method of this invention when no underground obstacles are present.
Figure 3:
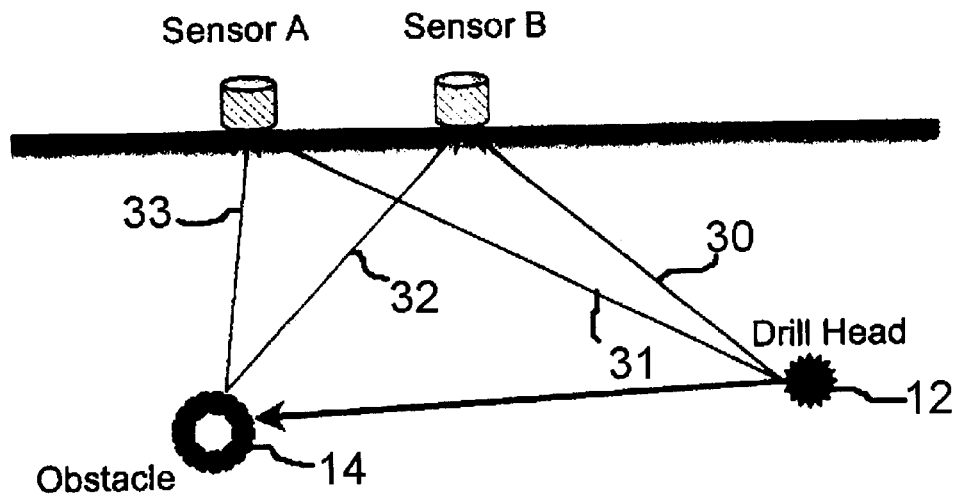
FIG. 3 is a diagram showing the principle of operation of the method of this invention when an underground obstacle is present.

The signal that is generated by the drill head is a wide band, noise-like signal. The exact characteristics cannot be controlled in detail, and the time of travel from the drill head to the sensors cannot be determined. However, the difference in arrival time at two or more sensors can be determined. If there are multiple paths, for example, a direct path 13 and a reflected path 15, 17 from an obstacle, the difference in travel time between these two paths can also be detected and measured. FIG. 2 is a diagram showing the situation in which no obstacle is present and FIG. 3 is a diagram showing the situation in which an obstacle is present. In the case shown in FIG. 2, the signal 20 arriving at the second sensor (sensor A) is a replica of the first signal 21 delayed in time arriving at the first sensor (sensor B). A cross-correlation of these two signals provides a peak at this time. In particular, if the two signals are $s_1(t)$ and $s_2(t)$, the cross-correlation is $$c(\tau) = \int_T s_1(t) s_2(t-\tau) dt$$

where c=cross-correlation between $s_1$ and $s_2$ $\tau$=difference in arrival time T=a time interval with the drill head operating $s_1$=signal from sensor 1

$s_2$=signal from sensor 2 t=time

The integral may be over a time interval of seconds providing very high signal-to-noise ratio compared with pulse-echo signals. The duty cycle of pulse-echo signals is typically 1%, whereas the cross-correlation is continuous (100% duty cycle).

In the case shown in FIG. 3, there are four signal paths: 1) drill head to sensor B 30; 2) drill head to sensor A 31; 3) drill head to obstacle to sensor B 32; and 4) drill head to obstacle to sensor A 33. The cross-correlation has peaks corresponding to the difference in propagation time for all of these signals. Those with the largest amplitudes are 1 and 2, 1 and 4, and 2 and 3. The peak corresponding to the difference between 3 and 4 is weaker. It can be detected by directional receivers that reject the direct wave from the drill head, but the preferred embodiment uses paths 1 and 4.

Figure 4:
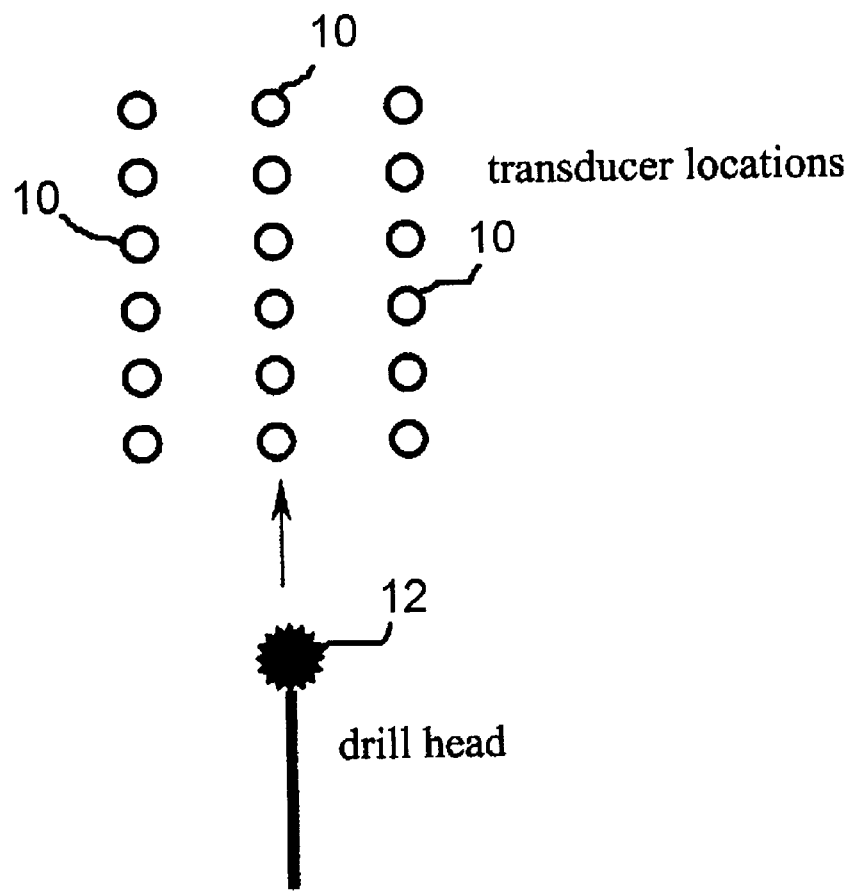
FIG. 4 is a diagram showing an exemplary 3 by 6 array of acoustic signal sensors and drill head suitable for use in the method of this invention.

In accordance with one preferred embodiment of this invention, a pattern of sensors is deployed along the guided drill path ahead of the drill as shown in FIG. 4. Although one row of sensors can be used, two or more rows provides sensitivity to pipes and other obstacles at skew angles to the drilling direction and, thus, are preferred. As the drill progresses through the soil, data is collected by amplifying and digitizing the acoustic signal in each acoustic signal sensor. The pass band is filtered to pass frequencies that reflect from the obstacle and reject frequencies that diffract past the obstacle. In the case of a pipe having a maximum diameter of d, any wavelength greater than $\pi$d (approximately 3d) will not reflect. The relationship between wavelength and frequency in soil is:

$$f\lambda = v$$

where f=sonic frequency (Hz)

$\lambda$=wavelength (cm)

v=sonic propagation velocity (cm/sec)

For example, if the pipe had a diameter of 30 cm, then wavelengths longer than 90 cm should be rejected. With a propagation velocity of 30,000 cm/sec, this corresponds to 30000/90=333 Hz. Thus, only frequencies higher than about 300 Hz should be processed.

Figure 5:
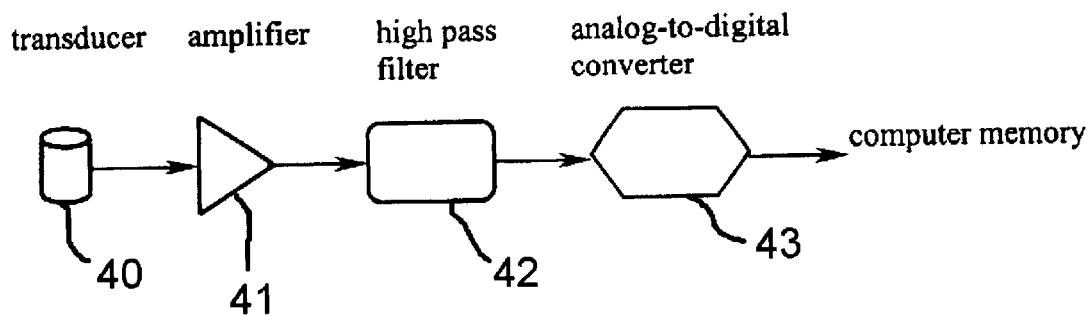
FIG. 5 is a diagram showing the path of data from the point of collection at the acoustic signal sensor to the data processor.
Figure 6:
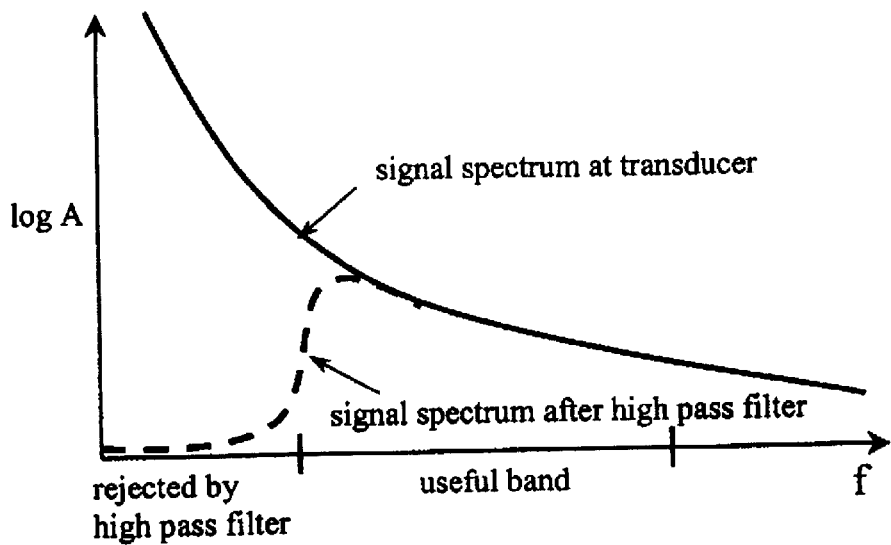
FIG. 6 is a diagram showing a sound spectrum of a signal received at an acoustic signal sensor.

The signal from each acoustic signal sensor 40 is processed in hardware according to the diagram showing FIG. 5. The signal is amplified by amplifier 41, then put through a high-pass filter 42 (300 Hz in this example) to eliminate parts of the spectrum that contain no useful echo information (FIG. 6). The output is digitized in an analog-to-digital converter 43 and sent to a computer for further analysis.

The spectrum of the sound is normally high at low frequencies and tapers to a low value at 3–5 kHz as shown in FIG. 6. A second normalization process is accomplished in software by applying a filter that provides a constant amplitude across the useful band of about 300 Hz to about 3 kHz in a typical case (FIG. 7). Then cross-correlations are taken between all acoustic signal sensor pairs. For example, FIG. 8A shows an array of 18 sensors, with 6 sensors disposed along the drill axis and 3 sensors disposed lateral to the axis. These sensors can be labeled $T_{ij}$ where i=1, 2, . . . 6 and j=1, 2, 3. For each j, all combinations of sets of $T_{ij}$ are analyzed to determine if an obstacle is detected. There are 15 pairs for each j as follows—1-2; 2-3; 3-4; 4-5; 5-6; 1-3; 2-4; 3-5; 4-6; 1-4; 2-5; 3-6; 1-5; 2-6; and 1-6.

FIG. 9 shows the cross-correlation when no obstacle exists. In this case, the direct wave time difference is 155 milliseconds. FIG. 10 shows the response with an obstacle in the beam. The time difference is 260 milliseconds between the direct wave and the obstacle. The times from different sensor pairs can be used to triangulate the position of the obstacle. A least squares triangulation of all data sets is used for the estimate.

If a detected signal occurs in some subset (for example, 4 in 15), a detection is declared. The difference in times for the direct signal is used to estimate to velocity (v) of propagation. This is:

$$v = \frac{d}{T}$$

where v=velocity estimate (cm/sec)

d=distance between transducers (cm); and

T=difference in arrival time (sec)

The differences in times for the reflection are used to estimate the position of the pipe. If the estimates from all j's are the same, then the pipe is normal to the drill direction.

Then, for each i, the j's are similarly analyzed. This process provides maximum sensitivity to pipes nearly parallel to the drill direction. Then, each diagonal is analyzed. These include patterns shown in FIGS. 8C and 8D. This provides sensitivity to pipes at skew angles.

While in the foregoing specification this invention has been described in relation to certain preferred embodiments, and many details are set forth for purpose of illustration, it will be apparent to those skilled in the art that this invention is susceptible to additional embodiments and that certain of the details described in this specification and in the claims can be varied considerably without departing from the basic principles of this invention.

We claim:

1. A method for detecting an underground obstacle comprising the steps of:

deploying a plurality of acoustic signal sensors in a predetermined pattern on an area of ground defined by a guided drill path having a drill head insertion point;

inserting a drill head of a drill into said ground at said drill head insertion point;

drilling a borehole in said ground along said guided drill path;

detecting a noise signal generated by said drill head at at least two of said plurality of acoustic signal sensors;

determining a difference in arrival time of said noise signal at said at least two of said plurality of acoustic signal sensors; and analyzing said difference in arrival time of said noise signal, whereby one of a presence and an absence of said underground obstacle is determined.

2. A method in accordance with claim 1, wherein a location of said underground obstacle relative to said drill head is determined.

3. A method in accordance with claim 1, wherein said plurality of acoustic signal sensors are deployed in a single row along said guided drill path.

4. A method in accordance with claim 1, wherein said plurality of acoustic signal sensors are deployed in at least two rows along said guided drill path.

5. A method in accordance with claim 1, wherein said noise signal received by each of said acoustic signal sensors is amplified, put through a high pass filter, and digitized in an analog-to-digital converter and conveyed to a processor for analysis.

6. A method in accordance with claim 1, wherein a cross-correlation of said noise signal received at said at least two of said plurality of acoustic signal sensors is performed.

7. A system for detecting an underground obstacle comprising:

at least one noise signal generator adapted for drilling boreholes in said ground along a guided drill path, said at least one noise signal generator being an only source of noise signal generated by said system;

a plurality of acoustic signal sensors disposed in a predetermined pattern on an area of ground defined by said guided drill path;

means for measuring an arrival time of said noise signal at each of said plurality of acoustic signal sensors; and obstacle means for determining one of a presence and an absence of said underground obstacle in said guided drill path using a difference in said arrival time of said noise signal between at least two of said plurality of acoustic signal sensors.

8. A system in accordance with claim 7, wherein said plurality of acoustic signal sensors are disposed in a single row along said guided drill path.

9. A system in accordance with claim 7, wherein said plurality of acoustic signal sensors are disposed in at least two rows along said guided drill path.

10. A system in accordance with claim 7, wherein said obstacle means comprises an amplifier having a sensor signal input operably connected to a sensor signal output of said plurality of acoustic signal sensors and an amplified signal output, a high-pass filter having an amplified signal input operably connected to said amplified signal output of said amplifier and a filtered signal output, an analog-to-digital converter having a filtered signal input operably connected to said filtered signal output of said high-pass filter and a digitized signal output, and a digitized signal processor suitable for analysis of said a digitized signal produced by said analog-to-digital converter operably connected to said digitized signal output of said analog-to-digital converter.

11. A system in accordance with claim 7, wherein said obstacle means comprises means for performing a cross-correlation of said noise signal received at said at least two of said plurality of acoustic signal sensors.

* * * * *